(12) United States Patent
Van De Bovenkamp-Bouwman et al.

(10) Patent No.: US 6,384,287 B1
(45) Date of Patent: May 7, 2002

(54) PEROXIDES, THEIR PREPARATION PROCESS AND USE

(75) Inventors: Anna Gerdine Van De Bovenkamp-Bouwman, Nijkerk; Bernhard De Vries, Nunspeet; John Meijer; Ejaz Ahmed Syed, both of Deventer; Andreas Herman Hogt, Enschede, all of (NL)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/762,671

(22) PCT Filed: Jul. 28, 1999

(86) PCT No.: PCT/EP99/05478

§ 371 Date: Apr. 18, 2001

§ 102(e) Date: Apr. 18, 2001

(87) PCT Pub. No.: WO00/09478

PCT Pub. Date: Feb. 24, 2000

(30) Foreign Application Priority Data

Aug. 12, 1998 (EP) .............................. 98202708

(51) Int. Cl.$^7$ ............................................. C07C 409/00
(52) U.S. Cl. ..................................................... 568/561
(58) Field of Search ............................... 568/558, 561, 568/567

(56) References Cited

U.S. PATENT DOCUMENTS

| | | | |
|---|---|---|---|
| 2,776,319 A | 1/1957 | Ropp | ..................... 260/610 |
| 3,575,920 A | * 4/1971 | Ballini et al. | |
| 3,576,826 A | 4/1971 | Bafford et al. | ............ 260/347.8 |

FOREIGN PATENT DOCUMENTS

| | | | |
|---|---|---|---|
| DE | 1 083 821 | 6/1960 | ......... C07C/120/27 |
| EP | 0 000 405 A1 | 1/1979 | ......... C07C/179/06 |
| GB | 1 263 593 | 2/1972 | ............ C07C/73/00 |

* cited by examiner

Primary Examiner—Jean F. Vollano
(74) Attorney, Agent, or Firm—Richard P. Fennelly

(57) ABSTRACT

The present invention relates to a new class of peroxides and to a process for the preparation of these peroxides having the general formula (I),

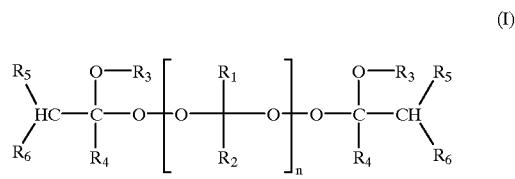

(I)

wherein n=1 or 2, $R_1$, $R_2$, $R_4$, $R_5$, and $R_6$ are independently selected from the group comprising hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, or $R_1$ and $R_2$ form a $C_3$–$C_{12}$ cycloalkyl group, which groups may include linear or branched alkyl moieties; and each of $R_1$, $R_2$, $R_4$, $R_5$, and $R_6$ may optionally be substituted with one or more groups selected from hydroxy, alkoxy, linear or branched alkyl, aryloxy, halogen, ester, carboxy, nitrile, and amido, and $R_1$ and $R_2$ may form a ring, and $R_3$ is independently selected from the group comprising $C_1$–$C_{20}$, alkyl; $C_3$–$C_{20}$ cycloalkyl, $C_6$–$C_{20}$ aryl, $C_7$–$C_{20}$, aralkyl, and $C_7$–$C_{20}$ alkaryl, which groups may include linear or branched alkyl moieties; and $R_3$ may optionally be substituted with one or more groups selected from hydroxy, alkoxy, linear or branched alkyl, aryloxy, halogen, ester, carboxy, nitrile, and amido, and any pair of the optionally substituted $R_3$, $R_4$, $R_5$, and $R_6$ may form a ring, comprising the reaction of the corresponding ketone.

16 Claims, No Drawings

PEROXIDES, THEIR PREPARATION PROCESS AND USE

This is the national phase of PCT EP99/05478, filed Jul. 28, 1999, now WO 00/09478.

The present invention relates to particular peroxides, their preparation process, and their use. More particularly, the present invention relates to the preparation process of these peroxides, which are obtainable by the reaction of a corresponding ketone peroxide and an alkyl vinyl ether or an acetal. Finally, the present invention relates to the use of these peroxides as polymerization initiators, curing agents for unsaturated polyesters, and modifying agents, and to formulations comprising these peroxides.

U.S. Pat. No. 3,576,826 discloses ether peroxy compounds and their preparation from alpha-substituted vinyl ether. In the class of ether peroxides (v) the adjacent peroxide groups may be separated by an unidentified aliphatic or cycloaliphatic group.

It is an object of the present invention to provide a new class of peroxides which are useful as polymerization initiators, curing agents for unsaturated polyesters, and modifying agents.

It is another object of the invention to provide peroxides with a higher reactivity in view of compounds of U.S. Pat. No. 3,576,826.

It is a further object of the invention to provide peroxides with a better storage stability at room temperature in view of compounds of U.S. Pat. No. 3,576,826.

Accordingly the present invention provides a process for the preparation of a peroxide having the general formula (I),

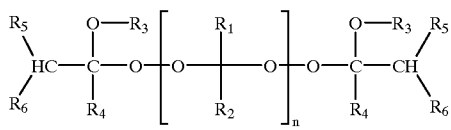
(I)

wherein n=1 or 2, $R_1$, $R_2$, $R_4$, R5, and $R_6$ are independently selected from the group comprising hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, or $R_1$ and $R_2$ form a $C_3$–$C_{12}$ cycloalkyl group, which groups may include linear or branched alkyl moieties; and each of $R_1$, $R_2$, $R_4$, $R_5$, and $R_6$ may optionally be substituted with one or more groups selected from hydroxy, alkoxy, linear or branched alkyl, aryloxy, halogen, ester, carboxy, nitrile, and amido, and $R_1$ and $R_2$ may form a ring; and $R_3$ is independently selected from the group comprising $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties; and $R_3$ may optionally be substituted with one or more groups selected from hydroxy, alkoxy, linear or branched alkyl, aryloxy, halogen, ester, carboxy, nitrile, and amido, and any pair of the optionally substituted $R_3$, $R_4$, $R_5$, and $R_6$ may form a ring, comprising the reaction of the corresponding ketone peroxide with the general formula (II)

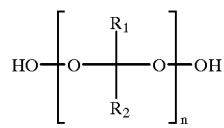
(II)

wherein n, $R_1$, and $R_2$ have the identified meaning, with an alkyl vinyl ether with the general formula (IIIa) or with an acetal with the general formula (IIIb)

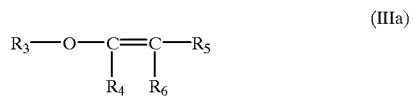
(IIIa)

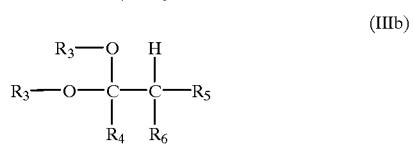
(IIIb)

wherein $R_3$, $R_4$, $R_5$, and $R_6$ have the identified meaning, in the presence of a catalyst.

The ketone peroxide of formula II may be a so-called $T_4$-ketone peroxide (n=1) and/or a so-called $T_3$-ketone peroxide (n=2).

The $T_4$-ketone peroxides having general formula IIa

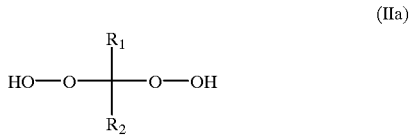
(IIa)

which are suitable for the reaction with said alkyl vinyl ether of formula IIIa or with said acetal of formula IIIb are those formed from the following ketones: acetone, acetophenone, methyl-n-amyl ketone, ethylbutyl ketone, ethylpropyl ketone, methylisoamyl ketone, methylheptyl ketone, methylhexyl ketone, ethylamyl ketone, diethylketone, dipropyl ketone, methylethyl ketone, methylisobutyl ketone, methylisopropyl ketone, methylpropyl ketone, methyl-n-butyl ketone, methyl-t-butyl ketone, methyl cyclohexanone, isobutylheptyl ketone, diisobutyl ketone, methoxy acetone, cyclohexanone, 3,3,5-trimethyl cyclo hexanone, N-butyllevulinate, ethylacetoacetate, methylbenzyl ketone, phenylethyl ketone, methylchloromethyl ketone, methylbromomethyl ketone; also other ketones having the appropriate $R_1$ and $R_2$ groups corresponding to the peroxides of the formula II can be employed, as well as mixtures of two or more different ketones.

The $T_3$-ketone peroxides having the general formula IIb

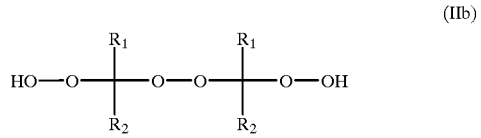
(IIb)

which are suitable for the reaction with said alkyl vinyl ether of formula IIIa or said acetal IIIb are those that are derived from the same group of ketones as mentioned for the $T_4$-ketone peroxides.

Preferably, the ketone peroxide is formed or derived from methylethyl ketone, methylisopropyl ketone, methylisobutyl ketone, acetone, cyclohexanone and/or 3,3,5-trimethylcyclohexanone. Methyl isobutyl ketone and methyl ethyl ketone are most preferable.

The alkyl vinyl ethers of formula IIIa (in which $R_4$ is hydrogen) may be exemplified as follows: vinyl 2,2-bis(vinyloxymethyl)butyl ether, allyl 2,3-epoxypropyl ether, n-propyl vinyl ether, 1-ethoxy-4-methyl-1-nonene, tert.amyl vinyl ether, 2,2-bis (4-vinyloxyphenyl) propane, hexadecyl vinyl ether, methyl vinyl ether, 4-methylhexyl vinyl ether, 2-(2-ethoxyethoxy)ethyl vinyl ether, 2-methoxyethyl vinyl ether, 2-vinyloxy ethanol, 4-methyl-1-decenyl vinyl ether, benzyl 1-methyl vinyl ether, butanediol divinyl ether, tert.butyl vinyl ether, isobutyl vinyl ether, cyclohexanedimethanol divinyl ether, cyclohexyl vinyl ether, ethyleneglycol divinyl ether, 1-ethoxy-4-(1-ethoxyvinyl)-3,3,5,5-tetramethylcyclohexene, allyl vinyl ether, isopropyl vinyl ether, ethyl vinyl ether, tetraethyleneglycol divinyl ether, 1-methoxy-1-buten-3-yne, heptyl vinyl ether, 4-(1-ethoxyvinyl)-3,3,5,5-tetramethylcyclohexanone, 2-butoxyethyl vinyl ether, allyl ethyl ether, divinyl ether, 1,3-divinyloxy-2,2-dimethylpropane, 4-vinyloxybutanol, diethyleneglycol divinyl ether, 4-(vinyloxymethyl) cyclohexylmethanol, isopentyl vinyl ether, diethyleneglycol monovinyl ether, n-butyl vinyl ether, 1,4-bis(2-vinyloxyethyl)benzene, hexanediol divinyl ether, 1-methoxy-1,3-butadiene, decyl vinyl ether, 4-(allyloxymethyl)-1,3-dioxolan-2-one, 1,1-diethylpropyl vinyl ether, 2-methoxyvinyl benzene, octyl vinyl ether, bis(vinyloxy)methane, 1,4-dimethoxy-1,3-butadiene, triethyleneglycol divinyl ether, pentyl vinyl ether, octadecyl vinyl ether, triethyleneglycol methyl vinyl ether, 2,3-epoxypropyl vinyl ether, dodecyl vinyl ether, 1,1-bis(vinyloxy)butane, hexyl vinyl ether, 6-vinyloxyhexanol, (z)-1-methoxy-1-buten-3-yne, phenyl vinyl ether, 2-ethylhexyl vinyl ether, poly-THF-divinyl ether, pluriol-E-200-divinyl ether, trimethylolpropane trivinyl ether, aminopropyl vinyl ether, 2-diethylaminoethyl vinyl ether, ethyl propenyl ether.

Examples of alkyl vinyl ethers of formula IIIa in which $R_4$ is alkyl are as follows: 2-methoxy-2 butene, 1,1,3-trimethoxypropene, 2,3-dimethoxy-1,3-butandiene, 2-methoxypropene, 2-ethoxy propene, 2-isobutoxypropene, 2-ethoxy-2-butene, 2-isobutoxy-2-propene.

Examples of tri-substituted and cyclic alkyl vinyl ethers are 1-methoxy-2-methyl cyclohexene and 2-methoxy-2-methyl-2-butene. Examples of the cyclic alkyl vinyl ethers are 2-methyl-2,3-dihydrofuran, 2,3-dihydrofuran, 2-methyl-3,4-dihydropyran, 3,4-dihydropyran, 1-methoxy cyclohexene. Preferred are ethyl vinyl ether, isobutyl vinyl ether, propyl vinyl ether, and butyl vinyl ether. Most preferred is isobutyl vinyl ether.

Examples of acetals of formula IIb are 2,2-dimethoxypropane, 2,2-diethoxypropane (with $R_4$ is alkyl) or, 1,1-dimethoxybutane, 2-propyl-1,3-dioxolane, 1,1-dimethoxyethane, 1,1-diethoxyethane, 1,1-diethoxypropane, and 1,1-dimethoxycyclohexane (with $R_4$ is hydrogen). Preferred is 1,1-dimethoxyethane.

The reaction between the ketone peroxide of formula II and the alkyl vinyl ether of formula IIIa or acetal of formula IIIb is carried out under conditions conventional for this type of addition reaction. The temperature generally is in the range of 0–50° C. and preferably is between 1–25° C. The reaction is carried out in the presence of an acid catalyst. The amount of acid catalyst generally is 0.01–30 g/mole and preferably 0.1–15 g/mole of ketone peroxide.

The acid catalyst for the process is a conventional acidic catalyst such as a $C_1$–$C_{10}$ alkane or aryl sulphonic acid, a halogenated $C_1$–$C_{10}$ alkane sulphonic acid or a mixture of one or more of these compounds. The preferred catalysts for use are, but are not limited to, p-toluenesulfonic acid and methane sulfonic acid. Although this reaction may be carried out without a solvent, it is preferred to carry out the reaction in a conventional homogenous solvent system.

Suitable solvents generally are hydrocarbon solvents, esters, aromatic hydrocarbon solvents, aralkyl solvents, paraffinic oils, white oils, and silicone oils, as well as their mixtures. Useful solvents include, but are not limited to, benzene, xylene, toluene, mesitylene, hexane, hydrogenated oligomers of alkanes such as Isopar$^R$ products (ex. Exxon), Shellsol$^R$ products (ex Shell), pentane, heptane, decane, isododecane, decalin, dibutyl phthalate, dioctyl adipate, dioctyl terephthalate, 2,2,4-tri methyl-1,3-pentanediol diisobutyrate, butylbenzoate, and the like. Among the paraffinic oils useful as solvents is paraffinic diesel oil. Other oils, including white oils, epoxidized soybean oils, and silicone oils are also useful in the present invention.

Preferably, $R_4$ is hydrogen because the peroxides show a better storage stability at ambient temperature and are less sensitive to hydrolysis. More preferably, $R_4$ and $R_5$ and/or $R_6$ are hydrogen.

Generally, the preparation process of the peroxide is carried out such that an equivalent amount of the alkyl vinyl ether of formula IIIa or of the acetal of formula IIIb is in the range of 1–5 equivalents. Preferably, the range is from 1.5 to 3.0 equivalents, more preferably from 2.0 to 2.5 equivalents. These numbers of equivalents are selected such that the chemical yield is optimal.

It is noted that in the preparation process the ketone peroxide used may be pure ($T_4$) ketone peroxide of formula IIa or ($T_3$) ketone peroxide of formula IIb. For specific properties it may be recommendable to use a mixture of $T_4$- and $T_3$-ketone peroxides. For instance, the $T_3$- or $T_4$-ketone peroxide may comprise 5%–30%, e.g., 5%–25% and 10%–15%, of the other ketone peroxide.

Furthermore, the invention relates to the peroxides of formula I

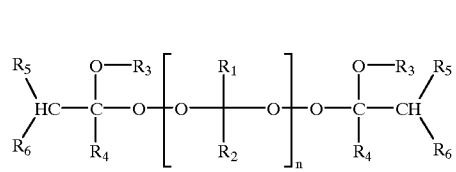

(I)

wherein $R_1$, $R_2$, $R_3$, $R_4$, $R_5$, and $R_6$ have the identified meaning and which are obtainable with the above-described preparation process.

The peroxides according to the present invention produced with the preparation processes according to the present invention may be used as initiators for polymer production and in particular for the preparation of poly (vinylchloride), acrylic (co)polymers, polystyrene, polyethylene, for curing unsaturated polyester resins, and for polymer modification (such as grafting of monomers).

In the present invention, the polymerization is conducted by any conventional process, except that a specified radical polymerization initiator (or composition) is used. The polymerization processes may be carried out in the usual manner, for example in bulk, suspension, emulsion or solution. In the case of the production of ethylene (co)polymers, the reaction is usually carried out under high pressure, e.g. about 1000 to about 3500 bar.

The amount of initiator, which varies depending on the polymerization temperature, the capacity for removing the heat of polymerization, and, where applicable, the kind of monomer to be used, and the applied pressure, should be an effective amount for achieving polymerization. Usually, from 0.001–25 wt. % of peroxide, based on the weight of the (co)polymer, is employed. Preferably, from 0.001–20 wt % of peroxide is employed and most preferably from 0.001–15 wt. %.

For most reactions within the present invention the polymerization temperature usually is 30° to 350° C., preferably 40° to 300° C. In general, if the temperature is below 30° C., the polymerization time becomes too long. However, when it exceeds 350° C., the radical polymerization initiator is spent in the initial stage of the polymerization, making it difficult to attain a high conversion. In order to reduce the amount of unreacted monomer, however, it is also possible to conduct the polymerization using a temperature profile, e.g., to perform the initial polymerization at below 100° C. and then elevate the temperature above 100° C. to complete the polymerization. These variations are all known to the man skilled in the art, who will have no difficulty selecting the reaction conditions of choice, depending on the particular polymerization process and the specific radical polymerization initiator to be used.

Suitable monomers for polymerization using the peroxides according to the present invention are olefinic or ethylenically unsaturated monomers, for example substituted or unsubstituted vinyl aromatic monomers, including styrene, alpha-methylstyrene, p-methylstyrene, and halogenated styrenes; divinylbenzene; ethylene; ethylenically unsaturated carboxylic acids and derivatives thereof, such as (meth)acrylic acids, (meth)acrylic esters, butyl acrylate, hydroxyethyl (meth)acrytate, methyl(meth)acrylate, 2-ethyihexyl (meth)acrylate, and glycidyl methacrylate; ethylenically unsaturated nitriles and amides, such as acrylonitrile, methacrylonitrile, and acrylamide; substituted or unsubstituted ethylenically unsaturated monomers, such as butadiene, isoprene, and chloroprene; vinyl esters, such as vinyl acetate and vinyl propionate; ethylenically unsaturated dicarboxylic acids and their derivatives including mono- and diesters, anhydrides, and imides, such as maleic anhydride, citraconic anhydride, citraconic acid, itaconic acid, nadic anhydride, maleic acid, fumaric acid, aryl, alkyl and aralkyl citraconimides and maleimides; vinyl halides, such as vinyl chloride and vinylidene chloride; vinyl ethers, such as methylvinyl ether and n-butyl vinyl ether; olefins, such as isobutene and 4-methylpentene; allyl compounds, such as (di)allyl esters, for example diallyl phthalates, (di)allyl carbonates, and triallyl (iso)cyanurate.

During (co)polymerization, the formulations may also contain the usual additives and fillers. As examples of such additives may be mentioned: stabilizers such as inhibitors of oxidative, thermal or ultraviolet degradation, lubricants, extender oils, pH controlling substances, such as calcium carbonate, is release agents, colourants, reinforcing or non-reinforcing fillers such as silica, clay, chalk, carbon black, and fibrous materials, such as glass fibers, plasticizers, diluents, chain transfer agents, accelerators, and other types of peroxides. These additives may be employed in the usual amounts.

Finally, the polymerization process of the present invention can be employed to introduce functional groups into the (co)polymers. This may be accomplished by employing a peroxide which contains one or more functional groups attached thereto. These functional groups remain intact in the free radicals formed by the peroxides and thus are introduced into the (co)polymer. Conventional polymerization conditions and equipment may be used to achieve this object of the present invention.

The peroxides according to the invention which may be used as a curing agent for the unsaturated polyesters and unsaturated polyester resins according to the present invention usually include an unsaturated polyester and one or more ethylenically unsaturated monomers. Suitable polymerizable monomers include styrene, alpha-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl (meth)acrylate, n-butyl (meth)acrylate, ethyl acrylate, and mixtures thereof which are copolymerizable with the unsaturated polyesters. The unsaturated polyesters are, for example, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, tetrahydrophthalic acid, and others, with saturated and unsaturated di- or polyols, such as ethylene glycol, diethylene glycol, triethylene glycol, 1,2- and 1,3-propane diols, 1,2-, 1,3-, and 1,4-butane diols, 2,2-dimethyl-1,3-propane diols, 2-hydroxymethyl-2-methyl-1,3-propane diol, 2-buten-1,4-diol, 2-butyn-1,4-diol, 2,4,4-trimethyl-1,3-pentane diol, glycerol, pentaerythritol, mannitol, and others. The di- or polycarboxylic acids may be partially replaced by saturated di- or polycarboxylic acids, such as adipic acid, succinic acid, and others, and/or by aromatic di- or polycarboxylic acids, such as phthalic acid, trimellitic acid, pyromellitic acid, isophthalic acid, and terephthalic acid. The acids used may be substituted with groups such as halogen. Suitable halogenated acids include, for example, tetrachlorophthalic acid and tetrabromophthalic acid.

The peroxides of the present invention are suited for use in the modification of polymers such as degradation, cross-linking or grafting. More particularly, these peroxides can be employed in processes for grafting monomers onto polymers such as polyolefins and elastomers, and for the functionalization of polyolefins in the case of functional group-containing peroxides of the present invention.

In general, the peroxide may be brought into contact with the (co)polymer in various ways, depending upon the particular object of the modification process.

The polymer material may be in the solid state, the molten state, in the form of a solution in the case of an elastomer, in a plastic state or in any physical form including finely divided particles (flakes), pellets, film, sheet, in the melt, in solution, and the like. Polymers may also be in the liquid form, e.g. liquid rubbers.

In general, any (co)polymer comprising abstractable hydrogen atoms, in particular polyolefins, can be modified by the present process.

The amount of peroxide used in the modification process of the present invention should be an effective amount for achieving significant modification of the (co)polymer when treating a (co)polymer. More particularly, from 0.001–15.0 wt. % of peroxide, based on the weight of the (co)polymer, should be employed. More preferably, from 0.005–10.0 wt. % percent is employed. Most preferably, an amount of 0.01–5.0 wt. % is employed.

The peroxides can be prepared, transported, stored, and applied in the form of powders, granules, pellets, pastilles, flakes, slabs, pastes, solid masterbatches, and liquids. These formulations may have the form of a dispersion, such as a suspension or an emulsion. They can be phlegmatized if necessary, depending on the particular peroxide and its concentration in the formulation. Which of these forms is to be preferred depends partly on the application for which it will be used and partly on the manner in which it will be mixed. Also, considerations of safety may play a role to the extent that phlegmatizers may have to be incorporated into certain compositions to ensure their safe handling.

The formulations of the present invention are transportable, storage stable, and contain 1.0–90 wt. % of one or more peroxides according to the present invention. Transportable means that the formulations of the present invention have passed the pressure vessel test (PVT). Storage stable means that the formulations of the present invention are both chemically and physically stable during a reasonable storage period under standard conditions.

Preferred formulations in accordance with the present invention contain 10–90 wt. % of one or more of the peroxides, more preferably these formulations contain 30–90 wt. % of the peroxides, most preferably these formulations contain 40–80 wt. % of the peroxides.

The formulations of the present invention can be liquids, solids or pastes, depending on the melting point of the peroxide and the diluent employed. Liquid formulations can be made using liquid phlegmatizers for the ketone peroxide, liquid plasticizers, organic peroxides, and mixtures thereof as the diluent. The liquid component generally is present in an amount of 1–99 Wt. % of the composition, preferably 10–90 wt. %, more preferably 30–90 wt. %, and most is preferably 40–80 wt. % of the liquid formulation consists of liquid diluents.

It should be noted that certain phlegmatizers may not be suitable for use with all of the peroxides of the present invention. More particularly, in order to obtain a safe composition, the phlegmatizer should have a certain minimum flash point and a boiling point relative to the decomposition temperature of the peroxide such that the phlegmatizer cannot be boiled off leaving a concentrated, unsafe ketone peroxide composition behind. Thus, the lower-boiling phlegmatizers mentioned below may only be useful, for example, with particular substituted peroxides of the present invention which have a low decomposition temperature.

In liquid formulations a liquid carder or diluent is used. Preferably, this carrier or diluent is a solvent. Examples of the solvents are those given above for the preparation of the various peroxides.

In the solid and/or paste formulations of the present invention solid carrier materials are employed. Examples of such solid carriers are low-melting solids, such as dicyclohexyl phthalate, dimethyl fumarate, dimethyl isophthalate, triphenyl phosphate, glyceryl tribenzoate, trimethyl olethane tribenzoate, dicyclohexyl terephthalate, paraffinic Waxes, dicyclohexyl isophthalate, polymers, and inorganic supports. Inorganic supports include materials such as fumed silica, precipitated silica, hydrophobic silica, chalk, whiting, surface-treated clays such as silane-treated clays, calcined clays, and talc.

Polymers useful in the formulations of the present invention include polyethylene, polypropylene, ethylene/propylene copolymers, ethylene/propylene/diene/monomer terpolymers, chlorosulphonated polyethylene, chlorinated polyethylene, polybutylene, polyisobutylene, ethylene/vinyl acetate copolymers, polyisoprene, polybutadiene, butadiene/styrene copolymers, natural rubber, polyacrylate rubber, butadiene/acrylonitrile copolymers, acrylonitrile/butadiene/styrene terpolymers, silicone rubber, polyurethanes, polysulphides, solid paraffins, and polycaprolactone.

Storage stable formulations must be both physically and chemically stable. By physically stable formulations are meant those formulations which do not suffer from significant phase separation upon storage. The physical stability of the present formulations can, in some instances, be improved by the addition of one or more thixotropic agents selected from cellulose esters, hydrogenated castor oil, and fumed silica. Examples of such cellulose esters are the reaction products of cellulose and acid compounds selected from, for example, acetic acid, propionic acid, butyric acid, phthalic acid, trimellitic acid, and mixtures thereof.

By chemically stable formulations are meant those formulations which do not lose a significant amount of their active oxygen content upon storage. The chemical stability of the present formulations can, in some instances, be improved by the addition of one or more known additives including sequestering agents such as dipicolinic acid and/or antioxidants such as 2,6-di(t-butyl)4-methyl phenol and para-nonyl phenol.

The formulations of the present invention may also contain optional other additives as long as these do not have a significant adverse effect on the transportability and/or storage stability of the formulations. As examples of such additives may be mentioned: anti-caking agents, free-flowing agents, anti-ozonants, anti-oxidants, anti-degradants, U.V. stabilizers, coagents, fungicides, antistats, pigments, dyes, coupling agents, dispersing aids, blowing agents, lubricants, process oils, and mold-release agents. These additives may be employed in their usual amounts.

The peroxides according to the invention may also be used as a dispersion, preferably in a polar medium. The medium in which the initiator according to the invention is dispersed should be inert towards the initiator and so polar that the initiator will hardly dissolve in it. The initiator preferably is dispersed in water or an alcohol. Most preferable is a dispersion in water. The use of such a medium makes for comparatively easy removal of any remnant, for example after the modification of the (co)polymer if so desired. Furthermore, the use of water or alcohols is attended with far fewer organoleptic and other drawbacks than the use of organic diluents, such as toluene and xylene, which has been common up to now.

As is well-known to the skilled person, the use of other adjuvants in initiator dispersions may be advisable or even essential in order to ensure the dispersion's chemical and/or physical stability for a sufficiently long period of time. For instance, if the storage temperature of the initiator dispersion is lower than the freezing point of the medium in which the initiator is dispersed, an appropriate freezing point depression agent can be added to counteract freezing. Also, a wide range of substances can be used for altering the rheology of the formulation. To this end generally use is made of one or more surface-active materials and one or more thickeners. If so desired, other additives may be incorporated into the formulation. As examples of such additives may be mentioned pH buffers, biocides, chemical stabilizers which counteract premature decomposition of the initiator, and anti-agers which counteract particle size growth in the dispersion.

The following examples illustrate the preparation processes for the peroxides according to the present invention and their applications.

EXAMPLE 1

Preparation of a mixture of 2.2.-bis(1-(1-methylpropoxy)ethylperoxy)butane and bis[1-methyl-1(1-(2-methylpropoxy)ethylperoxy)propyl]peroxide To a stirred solution of 25 g methylethyl ketone peroxide containing 27.82 wt. % 2,2-bis(hydroperoxy)butane T4 ketone peroxide and 14.4 wt. % bis(1-hydroperoxy-1-methylpropyl)peroxide T3 in dimethylphthalate was added 0.86 g p-toluene sulfonic acid monohydrate. Then 18.3 g isobutyl vinyl ether were added in 16 min, the reaction temperature being kept at 20° C. by cooling with an ice-water bath. The mixture was stirred for 2 min at 20° C. washed with bicarbonate solution, and dried over magnesium sulphate, yielding 41.6 g of product with an active oxygen content of 6.33% (chemical yield: 90%).

The following Table 1 shows the results of the preparation of other peroxides according to the invention ($R_1$=methyl; $R_4$, $R_5$, and $R_6$=H).

TABLE 1

| Example | R3 | R2 | n = 1:n = 2 Mole/mol | Solvent | Yield % | Active Oxygen (%) |
|---|---|---|---|---|---|---|
| 1a | Ethyl | Ethyl | 56:44 | Dimethyl-phthalate | 87 | 7.04 |
| 1b | Ethyl | Ethyl | 77:23 | Dimethyl-phthalate | 90 | 7.52 |
| 1c | Iso-butyl | Ethyl | 56:44 | Dimethyl-phthalate | 91 | 6.24 |
| 1d | Iso-butyl | Ethyl | 77:23 | Dimethyl-phthalate | 91 | 6.33 |
| 1e | Ethyl | Isobutyl | 16:84 | Pentadecane | 97 | 5.89 |
| 1f | n-propyl | Isobutyl | 43:57 | Isododecane | 93 | 6.53 |
| 1g | n-propyl | Isobutyl | 43:57 | Isododecane | 88 | 6.20 |
| 1h | Iso-butyl | Isobutyl | 43:57 | Isododecane | 90 | 6.41 |
| 1I | Iso-butyl | Isobutyl | 96:4 | Ethylacetate | 77 | 5.46 |
| 1j | Iso-butyl | Isobutyl | 0:100 | Isododecane | 70 | 6.26 |

EXAMPLE 2

Preparation of a mixture of 2,2-bis(1-methoxy-1-methylethylperoxy)4-methyl pentane and bis(1-(1-methoxy-1-methylethylperoxy)-1,3-dimethylbutyl) peroxide To a stirred solution of 50 g of methylisobutyl ketone peroxide containing 7.89 wt. % dihydroperoxy-1,3dimethylbutane and 36.84 wt. % bis(1-hydroperoxy-1,3-dimethylbutyl)peroxide in pentadecane was added 0.60 g acetic acid. Then 13.73 g 2-methoxypropene were added in 10 min, the reaction temperature being kept at 20° C. by cooling with an ice-water bath. The mixture was stirred for 30 min and 1.20 g of acetic acid were added. The mixture was allowed to stand overnight, yielding 65 g of product with an active oxygen content of 6.15%. Chemical yield: 97%.

EXAMPLE 3

Preparation of 1,1-bis(1-isobutoxyethylperoxy)cyclohexane

To a stirred solution of 30 g of 1,1-dihydroperoxycyclohexane in ethylacetate was added 0.4 g p-toluene sulfonic acid. Then 19.6 g isobutyl vinyl ether were added in 10 min, the reaction temperature being kept at 20° C. by cooling with an ice-water bath. The mixture was stirred for 60 min. The mixture was washed with sodium bicarbonate solution and dried on $MgSO_4$. Yield 35 g of product with an active oxygen content of 6.75% Chemical yield:67%.

EXAMPLE 4

Preparation of 2,2-bis(1-ethoxypropylperoxy)4-methyl pentane

To a stirred solution of 5 g of methyl isobutyl ketone peroxide containing 35.7 wt. % bis(1-hydroperoxy-1,3-dimethylbutyl)peroxide in isododecane was added 0.05 g p-toluene sulfonic acid. Then 1.8 g ethyl propenyl ether were added in 10 min, the reaction temperature being kept at 20° C. by cooling with an ice-water bath. The mixture was stirred for 20 min at 15° C. The mixture was washed with bicarbonate solution and dried over magnesium sulphate, yielding 5.8 g of product with an active oxygen content of 5.12% Chemical yield:91%.

EXAMPLE 5

Preparation of a mixture of 2,2-di(1-methoxybutylperoxy) butane and di(1-(1-methoxybutylperoxy)1-methylpropyl) peroxide.

To a stirred solution of 25 g methylethyl ketone peroxide, containing 27.82 wt. % 2,2-bis(hydroperoxy)butane and 14.4 wt. % bis(1-hydroperoxy-1-methylpropyl)peroxide in dimethyl phthalate was added 0.86 g p-toluene sulfonic acid monohydrate. Then 21.8 g 1,1-dimethoxybutane were added in 16 min, keeping the reaction temperature at 20° C. by cooling with an ice-water bath. The mixture was stirred 20 min more at 20° C., washed with bicarbonate solution, and dried over magnesium sulphate, yielding 35.2 g of product with an active oxygen content of 6.68%. (chemical yield: 90%).

EXAMPLE 6

Curing of unsaturated polyester

The curing performance of peroxides as curing agent for unsaturated polyester was determined and compared with tertiary butyl peroxy-2-ethyl hexanoate.

A time-temperature curve was measured at 100° C. on compounds containing 100 parts of polyester resin, 150 parts of sand as filler, and 1 part of peroxide. This was carried out according to the method outlined by the Society of Plastic Institute. 25 g of the compounds were poured into a test tube and a thermocouple was placed through the enclosure at the centre of the tube. The glass tube was then placed in the oil bath maintained at a specific test temperature and the time-temperature curve was measured. From the curve the following parameters were calculated.

Gel time (GT)=time in minutes elapsed between 16.7° C. below and 5.6° C. above the bath temperature.

Time to peak exotherm (TTP)=time elapsed between the start of the experiment and the moment that the peak temperature is reached. Peak exotherm (PE)=the maximum temperature which is reached. The results are shown in Table 2

TABLE 2

| Peroxide | Test temp. ° C. | GT min. | TTP. Min | PE ° C. |
|---|---|---|---|---|
| t-butyl peroxy-2-ethyl hexanoate | 100 | 0.87 | 3.4 | 197 |
| Example 1c | 100 | 2.17 | 5.57 | 184 |
| Example 1g | 100 | 0.78 | 3.38 | 197 |
| Example 1h | 100 | 0.67 | 3.22 | 195 |

EXAMPLE 7

High-solids acrylic resin synthesis

The suitability of the peroxides according to the invention for the production of high-solids acrylic resin was determined and compared with tert.butyl peroxy-2-ethyl hexanoate.

Polymerizations were conducted under nitrogen in a jacketed glass reactor equipped with a turbine stirrer, a thermocouple, a reflux condenser, and an injection inlet. The peroxide initiator was added to the monomers. This mixture was dosed to the solvent in a stirred vessel via the laboratory pump at the prescribed temperature in approx. 4 hours. The reaction was continued for an additional hour to reduce residual monomerlinitiator. From the resins obtained the molecular weights, colour, and percentage of solids were determined. The temperature was 165° C. The results are shown in Table 3.

TABLE 3

| Initiator | Initiator meq/100 g M | Solids content (%) | Mw (g/mol) | Mn (g/mol) | Disp. |
|---|---|---|---|---|---|
| Example 1 | 30 | 71.0 | 5400 | 2700 | 2.0 |
| t-butyl peroxy-2-ethyl hexanoate | 30 | 74.3 | 5400 | 2900 | 1.9 |

Recipe:

Monomers (in parts by weight)

n-butylacrylate (BA): 40 styrene (STY): 20

2-hydroxyethyl methacrylate (HEMA): 28 methyl methacrylate (MMA): 10 methacrylic acid (MA): 2

Solvesso 100 (S-100): 40 (solvent)

Initiator concentration: 30 meq/100 g monomers Temperature: 165° C.

Molecular weights were determined by gel permeation chromatography using polystyrene standards, according to method AR/94.14-1/HPLC obtainable from Akzo Nobel. Solids contents were determined by percentage of non-volatile matter (0.5 hour at 150° C.).

What is claimed is:

1. A process for the preparation of a peroxide having the formula (I),

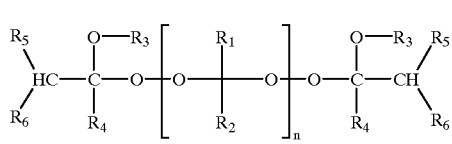

wherein n=1 or 2, $R_1$, $R_2$, $R_4$, $R_5$, and $R_6$ are independently selected from the group consisting of hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, or $R_1$ and $R_2$ form a $C_3$–$C_{12}$ cycloalkyl group, which groups may include linear or branched alkyl moieties; and each of $R_1$, $R_2$, $R_4$, $R_5$, and $R_6$, may optionally be substituted with one or more groups selected from hydroxy, alkoxy, linear or branched alkyl, aryloxy, halogen, ester, carboxy, nitrile, and amido, and $R_1$ and $R_2$, may form a ring, and $R_3$ is independently selected from the group consisting of $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties, and $R_3$ may optionally be substituted with one or more groups selected from hydroxy, alkoxy, linear or branched alkyl, aryloxy, halogen, ester, carboxy, nitrile, and amido, and any pair of the optionally substituted $R_3$, $R_4$, $R_5$, and $R_6$, may form a ring, comprising the reaction of the corresponding ketone peroxide with the formula (II)

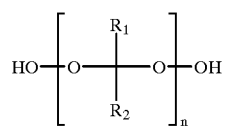

wherein n, $R_1$, and $R_2$ have the identified meaning, with an alkyl vinyl ether with the formula (IIIa) or with an acetal with the formula (IIIb)

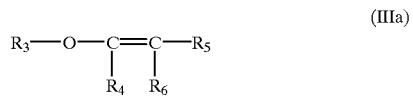

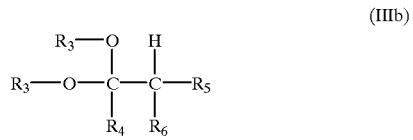

wherein $R_3$, $R_4$, $R_5$, and $R_6$, in the presence of a catalyst.

2. A process as claimed in claim 1, wherein $R_4$ is hydrogen.

3. A process as claimed in claim 1 wherein $R_5$ and/or $R_6$ are hydrogen.

4. A process as claimed in claim 1 wherein the equivalent amount of the alkyl vinyl ether (IIIa) or acetal (IIIb) is in the range of 1–5 equivalents.

5. A process as claimed in claim 1 wherein the ketone peroxide (IIa) is a mixture of the ketone peroxide having the formula (IIa),

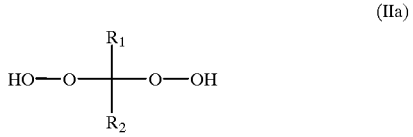

and of the ketone peroxide with the formula (IIb).

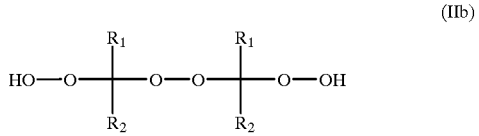

6. A process as claimed in claim 1 wherein the ketone peroxide is derived from methylethyl ketone, methylisopropyl ketone, methylisobuml ketone, acetone, cyclohexanone and/or 3,3,5-tnmethylcyclohexanone, preferably from methylisobutyl ketone or methylethyl ketone.

7. A process as claimed in claim 1 wherein the alkyl vinyl ether (IIIa) is selected from ethyl vinyl ether, isobutyl vinyl ether, propyl vinyl ether and butyl vinyl ether, preferably from isobutyl vinyl ether, or the acetal (IIIb) is selected from 2,2-dimethoxypropane, 2,2-diethoxypropane, 1,1-dimethoxybutane, 2-propyl-1,3-dioxolane, 1,1-dimethoxyethane, 1,1-diethoxyethane, 1,1-diethoxypropane, and 1,1-dimethoxycyclohexane.

8. A peroxide having the formula (I)

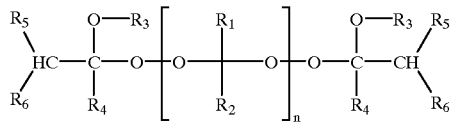

(I)

wherein n, $R_1$, $R_2$, $R_3$, $R_4$, $R_5$, and $R_6$ have the identified meaning as given in any of claims 1 to 3.

9. A formulation comprising a peroxide as claimed in claim 8, and a carrier or diluent.

10. A formulation as claimed in claim 9, comprising the peroxide in an amount of 1.0–99 wt. % and the carrier or diluent.

11. A formulation as claimed in claim 9 or 10 wherein the carrier or diluent is a solid, liquid or paste.

12. A formulation as claimed in any of claims 9 to 10 wherein the liquid is a polar solvent.

13. A formulation as claimed in any of claims 9 to 10 having the form of a dispersion.

14. A polymerization process wherein monomers are formed into a polymer by initiating the polymerization of the monomers with a peroxide as claimed in claim 8 to form the polymer.

15. A process for curing an unsaturated polyester by curing the unsaturated polyester with a peroxide as claimed in claim 8.

16. A process for the degradation, cross-linking or grafting of a polymer by degrading, cross-linking or grafting the polymer with a peroxide as claimed in claim 8.

* * * * *

UNITED STATES PATENT AND TRADEMARK OFFICE
CERTIFICATE OF CORRECTION

PATENT NO.   : 6,384,287 B1
DATED        : May 7, 2002
INVENTOR(S)  : Van de Bovenkamp-Bouwman et al.

It is certified that error appears in the above-identified patent and that said Letters Patent is hereby corrected as shown below:

<u>Column 12,</u>
Line 56, "methylisobum1" before "ketone" should read -- methylisobutyl --

Signed and Sealed this

Ninth Day of July, 2002

Attest:

Attesting Officer

JAMES E. ROGAN
Director of the United States Patent and Trademark Office